United States Patent
Peraus et al.

(10) Patent No.: US 6,673,600 B2
(45) Date of Patent: Jan. 6, 2004

(54) TRANSGENIC C. ELEGANS AS A MODEL ORGANISM FOR INVESTIGATIONS ON ALZHEIMER'S DISEASE

(75) Inventors: Gisela Peraus, München (DE); Edmund Hoppe, Krailing (DE); Ralf Baumeister, Gröbenzell (DE)

(73) Assignee: Aventis Pharma Deutschland GmbH, Frankfurt am Main (DE)

( * ) Notice: Subject to any disclaimer, the term of this patent is extended or adjusted under 35 U.S.C. 154(b) by 0 days.

(21) Appl. No.: 09/422,569

(22) Filed: Oct. 21, 1999

(65) Prior Publication Data

US 2003/0023997 A1 Jan. 30, 2003

(30) Foreign Application Priority Data

Oct. 24, 1998 (DE) .......................... 198 49 073

(51) Int. Cl.$^7$ ......................... C12N 15/00; C07H 21/02; C07H 21/04
(52) U.S. Cl. .................. 435/320.1; 536/23.1; 536/23.5; 536/24.1
(58) Field of Search .............................. 536/23.5, 23.1, 536/24.1; 435/320.1, 325, 69.1, 69.7, 455; 800/13

(56) References Cited

U.S. PATENT DOCUMENTS 5,744,346 A * 4/1998 Chrysler et al. ............ 435/226
5,849,999 A * 12/1998 Neve et al. ..................... 800/2

FOREIGN PATENT DOCUMENTS

WO    WO 98/16627     4/1998
WO    WO 98/28971   * 7/1998

OTHER PUBLICATIONS

Accession No. N90497; Jul., 1989.*
Accession No. V36456; Jun., 1998.*
Petitclerc; The effect of various introns and transcription terminators on the efficiency of expression vectors in various cultured lines and in the mammary gland of transgenic mice,1995, Journal of Biotechnology 40: 169–178.*
Link, C., Gene seq Accessioin No. V32663, Jul. 1998.*
Price et al., Annu. Rev. Genet., 32:461–493, 1998.*
Palmiter et al., Science, vol. No. 222, p. 809–814, Nov. 1983.*
Pursel et al., J. Reprod. Fert. Suppl. 40: 235–245, 1990.*
Kappel et al., Current Opinion in Biotechnology, 3:548–553, 1992.*
Expression of Human Beta–Amyloid Peptide in Transgenic Caenorhabditis Elegans, vol. 92, pp. 9368–9372, (1995),by Christopher D. Link.
Transgenic Caenorhabditis Elegans as Model System to Study Amyloid Formation and Toxicity, vol. 15, pp. 1, (1994), by Christopher D. Link.
Deposition of Beta/A4 Immunoreactivity and Neuronal Pathology in Transgenic Mice Expressing the Carboxyl–Terminal Fragment of the Alzheimer Amyloid Precursor in the Brain, vol. 89, pp. 10857–10861, (1992), by Kammesheidt et al.
Construction and Analysis of Transgenic Mice Expressing Amyloidogenic Fragments of Alzheimer Amyloid Protein Precursor, vol. 30, pp. 298–314, (1996), Neve et al.
Human Presenilin–I, But Not Familial Alzheimer's disease (FAD) Mutants, Facilitate Caenorhabditits Elegans Notch Signaling Independently of Proteolytic Processing, vol. 1, pp. 149–159, (1997), by Baumeister et al.
In Vivo Aggregation of Beta Amyloid Peptide Variants, vol. 71, pp. 1616–1625, (1998), by Fay et al.
Late Compartments of Amyloid Precursor Protein Transport in SY5Y Cells are involved in Beta–Amyloid Secretion, vol. 17, pp. 7714–7724, (1997), by Peraus et al.
Baumeister et al. (1997) Genes & Function 1, pp. 149–159.
Daigle et al., Proc. Natl. Acad. Sci. USA, vol. 90, pp. 12045–12049, Dec. 1993.
Haass et al., Chemical Abstract 130: 79392.
Kang et al., Nature vol. 325, Feb. 1987.
Cynthia Kenyon, (1988), Science, vol. 240, 1448.
Korswagen et al., Proc. Natl. Acad. Sci, USA, vol. 93, pp. 14680–14685.
Kuwabara, TIG Nov. 1997, vol. 13, No. 11.
Levitan et al., Nature, vol. 377, Sep. 28, 1995.
Levitan et al., Proc. Natl. Acad. Sci. USA, vol. 93, pp. 14940–14944, Dec. 1996.
Link, Proc. Natl. Acad. Sci. USA, vol. 92, pp. 9368–9372, Sep. 1995.
Maduro et al., Genetics 141: pp. 977–988, Nov., 1995.
Mello et al., The EMBO Journal, vol. 10, No. 12, pp. 3939–3970, 1991.
Mello et al., Methods in Cell Biology, Academic Press, vol. 48, pp. 451–483.
Ed. Epstein et al., "Modern Biological Analysis of an Organism", vol. 48, pp. 473–476.
Rumble et al., The New England Journal of Medicine, vol. 320, pp. 1446–1452.
Scheuner et al., Nature Medicine, vol. 2, No. 8, Aug. 1996, pp. 864–870.
Shoji et al., Science, vol. 258, Oct. 2, 1992, pp. 126–129.
Xiajun et al., Proc. Natl. Acad. Science, USA, 94, pp. 12204–12209.
Yankner et al., Proc. Natl. Acad. Science, USA, vol. 87, pp. 9020–9023, Nov. 1990.

* cited by examiner

*Primary Examiner*—Shin-Lin Chen
(74) *Attorney, Agent, or Firm*—Frommer Lawrence & Haug

(57) ABSTRACT

The present invention relates to a transgenic *C. elegans* which expresses an amyloid precursor protein (APP) or a part thereof, to the transgene itself, to the protein encoded by the transgene, and also to a process for preparing the transgenic *C. elegans* and to its use.

4 Claims, 2 Drawing Sheets

TRANSGENIC C. ELEGANS AS A MODEL ORGANISM FOR INVESTIGATIONS ON ALZHEIMER'S DISEASE

BACKGROUND OF THE INVENTION

1. Field of the Invention

The present invention relates to a transgenic *C. elegans* which expresses an amyloid precursor protein (APP) or a part thereof, to the transgene itself, to the protein encoded by the transgene, and also to a process for preparing the transgenic *C. elegans* and to its use.

2. Description of Related Art

Several publications are referenced in the application. These references describe the state of the art to which this invention pertains, and are incorporated herein by reference.

Alzheimer's disease (morbus Alzheimer) is a neurodegenerative disorder of the brain which, at the cellular level, is accompanied by a massive loss of neurons in the limbic system and in the cerebral cortex. At the molecular level, it is possible to detect protein depositions, so-called plaques, in the affected areas of the brain, which depositions constitute an important feature of Alzheimer's disease. The protein which most frequently occurs in these plaques is a peptide of from 40 to 42 amino acids in size which is termed the Aβ peptide. This peptide is a cleavage product of a substantially larger protein of from 695 to 751 amino acids, the so-called amyloid precursor protein (APP).

Figure 1:
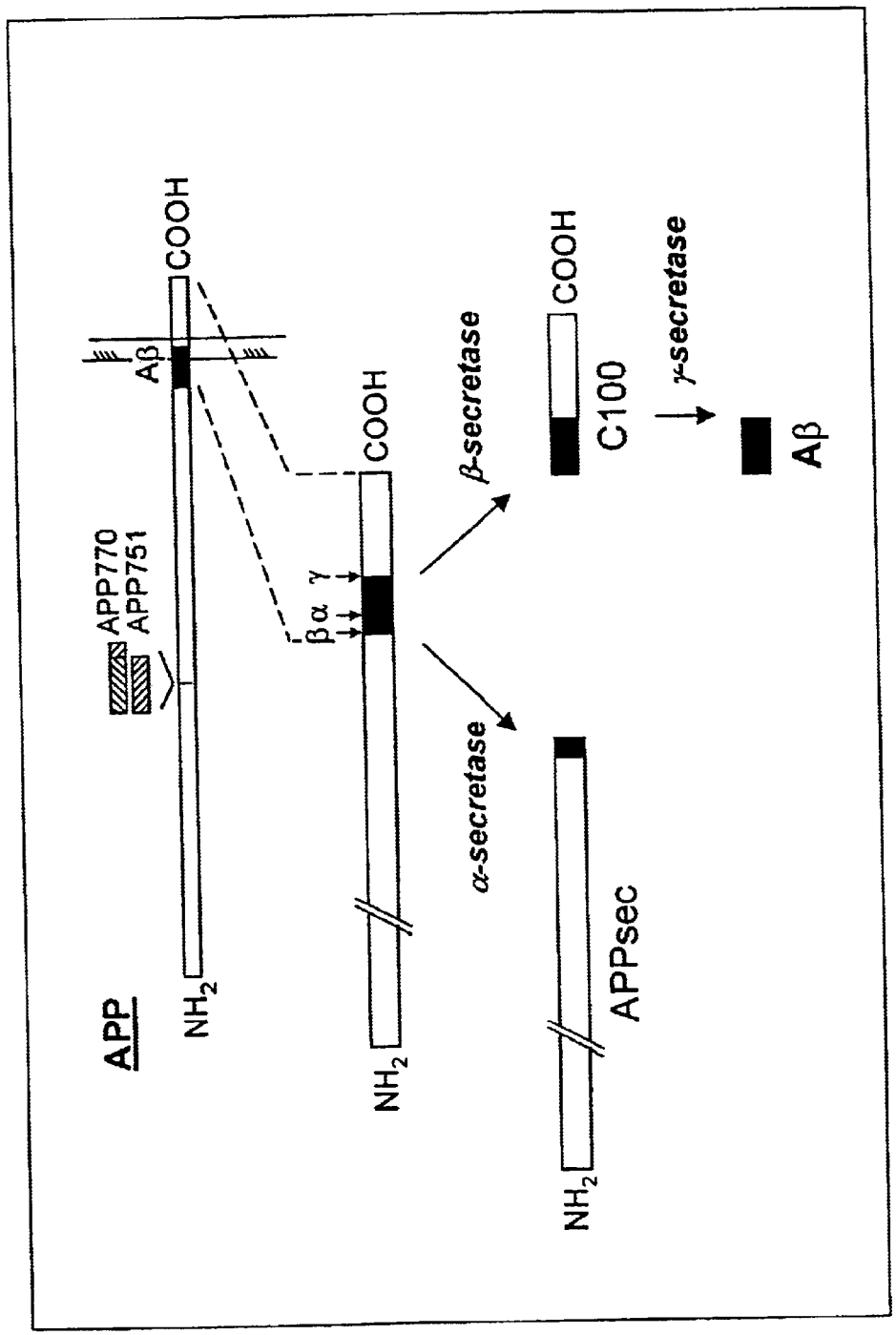

APP is an integral transmembrane protein which traverses the lipid double layer once. By far the largest part of the protein is located extracellularly, while the shorter C-terminal domain is directed into the cytosol (FIG. 1). The Aβ peptide is shown in dark gray in FIG. 1. About two thirds of the Aβ peptide are derived from the extracellular domain of APP and about one third from the transmembrane domain.

In addition to the APP which is located in the membrane, it is also possible to detect a secreted form of the amyloid precursor protein, which form comprises the large ectodomain of the APP and is termed APPsec ("secreted APP"). APPsec is formed from APP by proteolytic cleavage which is effected by α-secretase. The proteolytic cleavage takes place at a site in the amino acid sequence of APP which lies within the amino acid sequence of the Aβ peptide (after amino acid residue 16 of the Aβ peptide). Proteolysis of APP by the α-secretase consequently rules out the possibility of the Aβ peptide being formed.

The Aβ peptide can consequently only be formed from APP by an alternative processing route. It is postulated that two further proteases are involved in this processing route, with one of the proteases, which is termed β-secretase, cutting the APP at the N terminus of the Aβ peptide and the second protease, which is termed γ-secretase, releasing the C terminus of the Aβ peptide (Kang, J. et al., Nature, 325, 733) (FIG. 1).

It has not as yet been possible to identify any of the three secretases or proteases (α-secretase, β-secretase and γ-secretase). However, knowledge of the secretases is of great interest, in particular within the context of investigations with regard to Alzheimer's disease and with regard to identifying the proteins involved, which proteins can then in turn be employed as targets in follow-up studies since, on the one hand, inhibition of the β-secretase, and in particular of the γ-secretase, could lead to a decrease in Aβ production and, on the other hand, activation of the α-secretase would increase the processing of APP into APPsec and thereby simultaneously reduce formation of the Aβ peptide.

There is a large amount of evidence that the Aβ peptide is a crucial factor in the development of Alzheimer's disease. Inter alia, Aβ fibrils are postulated to be neurotoxic in cell culture (Yankner, B. A. et al., (1990) Proc Natl Acad Sci USA,87, 9020). Furthermore, the neuropathology which is characteristic of Alzheimer's disease already appears at the age of 30 in Down's syndrome patients, who have an additional copy of APP. In this case, it is assumed that overexpression of APP is followed by an increased conversion into the Aβ peptide (Rumble, B. et al., (1989), N. Engl. J. Med., 320,1446).

The familial forms of Alzheimer's disease constitute what is probably the most powerful evidence of the central role of the Aβ peptide. In these forms, there are mutations in the APP gene around the region of the β-secretase and γ-secretase cleavage sites or in two further AD-associated genes (presenilins) which, in cell culture, lead to a substantial increase in Aβ production (Scheuner, D. et al., (1996), Nature Medicine, 2, 864).

While *C. elegans* has already been used as a model organism in Alzheimer's disease, these studies do not relate to the processing of APP into the Aβ peptide. Some of the studies are concerned with two other Alzheimer-associated proteins, i.e. the presenilins. The presenilins are transmembrane proteins which traverse the membrane 6–8 times. They are of great importance in familial cases of Alzheimers since specific mutations in the presenilin genes lead to Alzheimer's disease. In this connection, it was shown that homologs to the human presenilins (sel-12, spe-4 and hop-1) are present in *C. elegans*, with the function of the presenilins being conserved in humans and worm (Levitan D, Greenwald I (1995) Nature 377, 351; Levitan et al.(1996) Proc Natl Acad Sci USA, 93, 14940; Baumeister R (1997) Genes & Function 1, 149; Xiajun Li and Iva Greenwald (1997) Proc Natl Acad Sci USA, 94, 12204).

Other studies deal with the APP homolog in *C. elegans*, which is termed Apl-1, and with expression of the Aβ peptide in *C. elegans*. However, Apl-1 does not possess any region which is homologous with the amino acid sequence of the Aβ peptide; *C. elegans* does not therefore possess any endogenous Aβ peptide (Daigle I, Li C (1993) Proc Natl Acad Sci USA, 90 (24), 12045).

C. D. Link, Proc Natl Acad Sci USA (1995) 92, 9368 described the expression of Aβ peptide (but not that of an Aβ precursor protein) in *C. elegans*. These studies involve preparing transgenic worms which express an Aβ1-42 peptide (i.e. the Aβ peptide which consists of 42 amino acids) as a fusion protein together with a synthetic signal peptide and under the control of the muscle-specific promoter unc 54. Muscle-specific protein depositions which reacted with anti-β-amyloid antibodies were detected in the studies.

Other studies (e.g. C. Link et al. personal communication) relate to investigations of the aggregation and toxicity of the Aβ peptide in the *C. elegans* model system.

Transgenic *C. elegans* lines were established in the present study in order to investigate the existence of a processing machinery in *C. elegans* which is involved in the formation of Aβ peptide and to identify potential secretases in this worm.

SUMMARY OF THE INVENTION

In this invention, APP genes have been transferred into *C. elegans* to create a transgenic *C. elegans* organism. This transgenic *C. elegans* can then be used to investigate the processing machinery involved in the formation of the Aβ peptide and to identify potential secretases.

The present invention relates to a transgene (a gene that has been transferred from one species to another by genetic engineering) which contains a) a nucleotide sequence encoding an amyloid precursor protein (APP) or a part thereof, wherein the nucleotide sequence comprising the APP peptide or part thereof, contains, as part of the sequence, a nucleotide sequence comprising a complete Aβ peptide or a part of the Aβ peptide, and b) where appropriate, one or more further coding and/or non-coding nucleotide sequences, and c) a promoter for expression in a cell of the nematode *Caenorhabditis elegans* (*C. elegans*).

The nucleotide sequence preferably encodes the 100 carboxyterminal amino acids of APP, beginning with the sequence of the Aβ peptide and ending with the carboxy-terminal amino acid of APP (C100 fragment). The APP is preferably one of the isoforms APP695 (695 amino acids), APP751 (751 amino acids), APP770 (770 amino acids) and L-APP. All the isoforms are formed from the same APP gene by means of alternative splicing. In APP695, exons 7 and 8 were removed by splicing, whereas only exon 8 is lacking in APP751 and exon 7 and 8 are present in APP770. In addition to this, other splicing forms of APP exist in which exon 15 has been removed by splicing. These forms are termed L-APP and are likewise present in the forms which are spliced with regard to exons 7 and 8.

In one particular embodiment of the invention, the transgene contains the nucleotide sequence SEQ ID NO.: 1 or a part thereof or a sequence homologous to SEQ ID No. 1.

The transgene can preferably contain an additional coding nucleotide sequence which is located at the 5' end of the nucleotide sequence encoding APP or a part thereof. In one particular embodiment of the invention, the additional nucleotide sequence encodes a signal peptide or a part thereof, for example encodes the APP signal peptide (SP) having the amino acid sequence SEQ ID NO.:9 or a part thereof. The sequence from the N terminus of the Aβ peptide to the C terminus of APP consists of 99 amino acids. The APP signal peptide consists of 17 amino acids. When a fusion product comprising the N terminus of the Aβ peptide to the C terminus of APP and the APP signal peptide is cloned, one or more spacer amino acids is/are preferably inserted between these two parts of the fusion product, with preference being given to inserting one amino acid, for example leucine. The C-terminal fragment is therefore given different designations, e.g. C100 (C=C terminus), LC99 (L=leucine), LC1-99, C99 or SPA4CT (SP=signal peptide, A4=Aβ peptide and CT=C terminus).

In one particular embodiment of the invention, the transgene contains the nucleotide sequence SEQ ID NO.: 2 or a part thereof and/or the nucleotide sequence SEQ ID NO.: 3 or a part thereof.

In addition to this, the transgene can also contain one or more additional non-coding and/or one or more additional coding nucleotide sequences.

For example, the transgene can contain, as an additional non-coding nucleotide sequence, a sequence from an intron of the APP gene, e.g. a sequence which is derived from the 42 bp intron of the APP gene and exhibits the sequence SEQ ID NO.: 4. A transgene which contains the nucleotide sequence SEQ ID NO.: 5 is part of the subject-matter of the invention.

The transgene also preferably contains one or more gene-regulating sequences for regulating expression of the encoded protein, preferably a constitutive promoter or a promoter which can be regulated. For example, the promoter can be active in the neuronal, muscular or dermal tissue of *C. elegans* or be ubiquitously active in *C. elegans*. A promoter can, for example, be selected from the group of the *C. elegans* promoters unc-54, hsp 16-2, unc-119, goa-1 and sel-12. In one particular embodiment of the invention, the transgene contains a promoter having the nucleotide sequence SEQ ID NO.: 6. In one particular embodiment, the transgene contains the nucleotide sequence SEQ ID NO.: 7.

The transgene can be present in a vector, for example in an expression vector. For example, a recombinant expression vector can contain the nucleotide sequence SEQ ID NO.: 8.

The invention also relates to the preparation of an expression vector, with a transgene being integrated into a vector in accordance with known methods. In particular, the invention relates to the use of an expression vector for preparing a transgenic cell, with it being possible for this cell to be part of a non-human organism, e.g. *C. elegans*.

The invention also relates to the preparation of the transgene, with suitable part sequences being ligated in the appropriate order and in the correct reading frame, where appropriate while inserting linkers. In particular, the invention relates to the use of the transgene, for example for preparing a transgenic cell, with it being possible for this cell to be part of a non-human organism. For example, the cell can be a *C. elegans* cell.

One particular embodiment of the invention relates to a transgenic *C. elegans* which contains the transgene. The transgene can also be present in the *C. elegans* in an expression vector. The transgene can be present in the *C. elegans* intrachromosomally and/or extrachromosomally. One or more transgenes or expression vectors which contain the transgene can be present intrachromosomally and/or extrachromosomally as long tandem arrays. A transgenic cell or a transgenic organism preferably contains another expression vector as well, which vector contains a nucleotide sequence which encodes a marker, with the marker either being a temperature-sensitive marker or a phenotypic marker. For example, the marker can be a visual marker or a behaviorally phenotypic marker. Examples are fluorescent markers, e.g. GFP (green fluorescent protein) or EGFP (enhanced green fluorescent protein), marker genes which encode a dominant, mutated form of a particular protein, e.g. a dominant Rol6 mutation, or marker sequences which encode antisense RNA, e.g. the antisense RNA of Unc-22.

One or more copies of the transgene and/or of the expression vector and, where appropriate, of an additional expression vector are preferably present in the germ cells and/or the somatic cells of the transgenic *C. elegans*.

Figure 2:
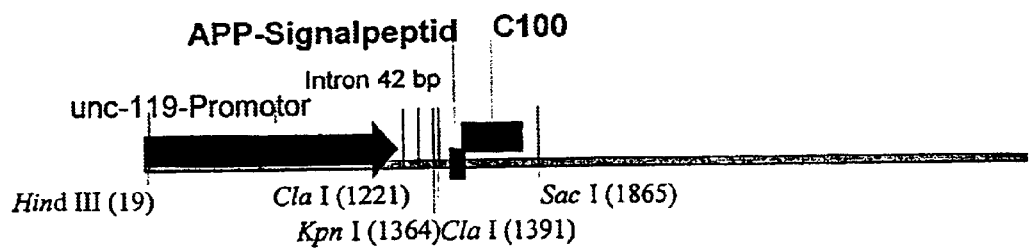

The invention also relates to a process for preparing a transgenic *C. elegans*, with a transgene and/or an expression vector, where appropriate in the presence of an additional expression vector which contains a nucleotide sequence which encodes a marker, being microinjected into the germ cells of a *C. elegans*. A DNA construct which expresses SP-C100 (SP=signal peptide) under the control of a neuron-specific promoter can, for example, be used for preparing the transgenic *C. elegans* lines (FIG. 2). Since C100 is composed of the Aβ sequence and the C terminus of APP, only the γ-secretase cleavage is required in order to release the Aβ peptide from C100. C100 is also a substrate for the γ-secretase.

The invention also relates to the use of a transgenic *C. elegans*, for example for expressing an SP-C100 fusion protein. An SP-C100 fusion protein having the amino acid sequence SEQ ID NO.: 10 is part of the subject-matter of the invention.

In particular, the invention relates to the use of a transgenic *C. elegans* for identifying a γ-secretase activity and/or an α-secretase activity in *C. elegans*, to its use in methods for identifying and/or characterizing substances which inhibit the γ-secretase activity, to its use in methods for identifying and/or characterizing substances which increase the α-secretase activity, and to its use in methods for identifying and/or characterizing substances which can be used as active compounds for treating and/or preventing Alzheimer's disease.

DESCRIPTION OF THE PREFERRED EMBODIMENTS

In the present study, the nematode *Caenorhabditis elegans* (*C. elegans*) was chosen as the model organism for identifying secretases which are involved in processing APP into the Aβ peptide. This worm is outstandingly suitable for genetic studies and has therefore in the past been employed on many occasions for investigating universally important processes such as programmed cell death, neuronal guidance and RAS/MAP kinase signaling (Riddle, D. L. et al. (1997)).

The important points which make *C. elegans* especially appropriate for such studies include the following (C. Kenyon, Science (1988) 240, 1448; P. E. Kuwabara (1997), TIG, 13, 454):

- Its small genome, which is composed of about 19,000 genes or 97 Mb and which was sequenced completely in December 1998. (The *C. elegans* Sequencing Consortium, Science (1998), 282, 2012).
- Its reproduction by self fertilization. In the case of the two sexes of *C. elegans*, a distinction is made between males and hermaphrodites, i.e. hermaphroditic animals which fertilize their eggs themselves before laying. A crucial advantage of this type of reproduction is that, after a transgene has been introduced into the germ line, a hermaphrodite can automatically generate homozygous transgenic descendants. There is therefore no need for any further crossing steps, as in the case of Drosophila, for example, for preparing transgenic lines.
- Its easy handling in the laboratory due to its small size (about 1 mm in length) and its relatively undemanding growth conditions. As a result, a large number of worms can be handled routinely in the laboratory.
- Its short generation time of 3 days, which makes it possible to obtain large quantities of biological material for analysis within a very short time.
- A complete cell description for the development and anatomy of *C. elegans* is available.
- Detailed genetic maps and methods for genetic analysis in *C. elegans* are available.
- Technologies for preparing knock-out animals are available. In the same way, technologies exist for mutagenizing the *C. elegans* genome (transposon mutagenesis and ethyl methanesulfonate (EMS) mutagenesis).

The following are possible uses of the transgenic *C. elegans* lines:

1. Identification of a γ-secretase-like activity in *C. elegans* using mutagenesis approaches. It is planned that a transposon mutagenesis, which destroys the γ-secretase-like activity, should be carried out and that the corresponding gene should be sought by detecting the worms which no longer possess this activity. Such a screening method is described in the literature: Korswagen H. C. et al., (1996), 93, 14680 Proc Natl Acad Sci USA.

Alternative approaches would be mutagenesis using ethyl methanesulfonate (EMS) or else anti-sense RNA approaches. In the latter case, an attempt could be made to find motifs which were common to all *C. elegans* proteases and to downregulate these proteases specifically using anti-sense RNAs which were directed against these motifs. Screening for the Aβ peptide could then show whether one of the proteases was involved in Aβ peptide production.

2. Identification of a γ-secretase-like activity in *C. elegans*, perhaps by a similar route to that described in item 1.

3. Armed with knowledge of a γ-secretase or γ-secretase-like activity in *C. elegans*, it is possible to search for human γ-secretase or γ-secretase-like activity by means of a homology comparison.

4. Identification of drugs which
   - inhibit the activity of γ-secretase, in order to inhibit Aβ production from the amyloid precursor protein directly.
   - activate γ-secretase and thereby indirectly inhibit formation of the Aβ peptide by increasing APPsec production.

This approach could take place in a 96-well format since *C. elegans* can be maintained in suspension in 96-well plates.

Since the screening is carried out on a whole organism, it is possible, to a large extent, to exclude drugs which have an unspecific toxic effect.

5. Investigation of the aggregation behavior, and of a possible neurotoxic effect, of the Aβ peptide in *C. elegans*. Screening for drugs which inhibit aggregation of the Aβ peptide.

6. Investigation of the modulation of APP processing by other proteins (e.g. presenilins or ApoE) as a result of their overexpression or knock-out. Since the presenilins are Alzheimer-associated proteins and ApoE constitutes a risk factor in Alzheimer's disease, these proteins could have an effect on formation of the Aβ peptide and, as a consequence, their role in the APP processing pathway could be investigated.

7. Where appropriate, validation of an α-secretase and/or γ-secretase activity which has been found using other experimental approaches known to the skilled person.

FIG. 1: FIG. 1 shows the amyloid precursor protein (APP695 isoform and APP770 and APP751 isoforms) and secretase cleavage products.

FIG. 2: FIG. 2 describes the construction of the transgenic vector "Unc-119-SP-C100", which contains an unc-119 promoter, an APP signal peptide and the C100 fragment from APP, with "unc-119" being a neuron-specific *C. elegans* promoter, the APP signal peptide corresponding to amino acids 1 to 24 of APP and C100 corresponding to the 100 C-terminal amino acids of APP (=C100). C100 is composed of the Aβ sequence and the C terminus of APP (Shoji, M et al., (1992) Science 258, 126). The vector Unc-119-SP-C100 possesses 5112 base pairs.

EXAMPLES

The following examples are illustrative of some of the products and compositions and methods of making and using the same falling within the scope of the present invention.

Example 1

Preparing an Expression Vector Which Contains the Transgene

Two vectors, i.e. pSKLC1-99, which encodes SP-C100, and pBY103, which contains the unc-119 promoter, were used for the cloning, with the SP-C100-encoding DNA being cloned into the pBY103 vector behind the unc-119 promoter. The basic vector pBY103 is composed of the vector backbone pPD49.26, which is described in "Caenorhabditis elegans: Modern Biological Analysis of an Organism" (1995) Ed. Epstein et al., Vol 48, pp. 473, into which the unc-119 promoter (Maduro et al. Genetics (1995), 141, p. 977) has been cloned by way of the HindIII/BamHI sites. The plasmid unc-119-SP-C100 was prepared by KpnI/SacI digestion of pSKLC1-99 and cloning of the LC99 fragment into pBY103 (Shoji et al. (1992).

Example 2

Preparing the Transgenic C. elegans Lines

The method of microinjection was used for preparing the transgenic C. elegans lines (Mello et al., (1991) EMBO J. 10 (12) 3959; C. Mello and A. Fire, Methods in Cell Biology, Academic Press Vol. 48, pp. 451, 1995; C. D. Link, Proc Natl Acad Sci USA (1995) 92, 9368).

Two different C. elegans strains, i.e. wild-type N2 and him-8 (high incidence of males), were used. The unc-119-SP-C100 construct was microinjected into the gonads of young adult hermaphrodites using a microinjection appliance. The DNA concentration was about 20 ng/µl.

A marker plasmid was injected together with the unc-119-SP-C100 construct. This marker plasmid is the plasmid ttx3-GFP, which encodes the green fluorescent protein under the control of the ttx3 promoter. The activity of the ttx3 promoter is specific for particular neurons of the C. elegans head, the so-called AIY neurons, which play a role in the thermotaxis of the worm.

When plasmid DNA is microinjected, it is assumed that long tandem arrays, which are composed of many copies of plasmid DNA (in our case, of the ttx3-GFP plasmid and the unc-119-SP-C100 plasmid), are formed by recombination. A certain percentage of these arrays integrate into the C. elegans genome. However, the arrays are more likely to be present extrachromosomally.

Worms which had been injected successfully exhibit a green fluorescence in the AIY neurons of the head region when stimulated with light of a wavelength of about 480 nm. It was possible to detect such nematodes.

Example 3

Describing the C100 Transgenic C. elegans Lines
1. Phenotypic Features

Following stimulation with light of a wavelength of 480 nm, C100-transgenic worms exhibit a green fluorescence in the AIY neurons of the head region. Since it was also possible to detect green fluorescence in the head neurons once again in the descendants of the worms, it can be assumed that the plasmids are able to pass down through the germ line. However, the penetrance is not 100%, which makes it possible to conclude that the long tandem arrays composed of ttx3-GFP marker DNA and unc-119-SP-C100 are present extrachromosomally rather than being integrated into the genome.

Example 4

Detecting C100 Expression in a Blot

Six different transgenic C100 C. elegans lines (three in an N2 wt background and three in a him 8 background) were examined in a Western blot for expression of the C100 fragment using a polyclonal antiserum directed against the C terminus of APP. A band having the appropriate molecular weight of about 10 kDa was detectable in all the six lines.

Example 5

Detecting the C100 in an ELISA

In an Aβ Sandwich ELISA, signals which were above the background level, and which were statistically significant in two cases, were detected in cell extracts from transgenic animals. This indicates that C. elegans could possess a γ-secretase-like activity.

In the Aβ Sandwich ELISA assay, 96-well plates are first of all incubated with the monoclonal antibody clone 6E10 (SENETEK PLC., MO, USA), which reacts specifically with the Aβ peptide (amino acids 1–17), and then coated with worm extracts from transgenic worms or control worms. The Aβ peptide is detected using the monoclonal Aβ antibody 4G8 (SENETEK PLC., MO, USA), which recognizes amino acids 17–24 in the Aβ peptide and is labeled with biotin. The detection is effected by way of the alkaline phosphatase reaction using an appropriate antibody which is directed against biotin. Disruption of the worms involves detergent treatment, nitrogen shock freezing, sonication and rupture of the cells using glass beads.

The ELISA signal from the above-described experiment can be based either on weak expression of the Aβ peptide or on expression of the C100 precursor protein, since the appropriate epitopes are present in both proteins.

Expression of the Aβ peptide could, for example, also be specifically detected in an analogous manner: for this, Aβ-specific antibodies which do not react with the C100 precursor would have to be employed in an Aβ Sandwich ELISA. An Aβ-specific antibody could, for example, be a monoclonal antibody which specifically recognizes the C-terminal end of the Aβ form, which is composed of 40 or 42 amino acids. In parallel, the Aβ peptide could be detected in a Western blot using the monoclonal antibodies 4G8 and 6E10 and then be distinguished from the larger C100 precursor by its molecular weight of 4 kD.

The vectors can be obtained from Andrew Fire (Department of Embryology, Carnegie Institution of Washington, Baltimore, Md. 21210, USA) in the case of pPD49.26 and LC99 (amyloid precursor protein), which is deposited under ATCC number 106372. The unc-119 promoter can be obtained from Maduro, M. (Department of Biological Science, Universitiy of Alberta Edmonton, Canada), while unc-54 and unc-16.2 can be obtained from Andrew Fire.

The above description of the invention is intended to be illustrative and not limiting. Various changes or modifications in the embodiments described may occur to those skilled in the art. These can be made without departing from the spirit or scope of the invention.

SEQ ID NO.1: Nucleotide sequence of C100

CTGGATGC AGAATTCCGA CATGACTCAG GATATGAAGT TCATCATCAAAAATTGGTGT

TCTTTGCAGA AGATGTGGGT TCAAACAAAG GTGCAATCAT TGGACTCATGGTGGGCGGTG

TTGTCATAGC GACAGTGATC GTCATCACCT TGGTGATGCT GAAGAAGAAACAGTACACAT

CCATTCATCA TGGTGTGGTG GAGGTTGACG CCGCTGTCAC CCCAGAGGAGCGCCACCTGT

CCAAGATGCA GCAGAACGGC TACGAAAATC CAACCTACAA GTTCTTTGAGCAGATGCAGA ACTAG

SEQ ID NO.2: Nucleotide sequence of SP

ATG CTGCCCGGTT TGGCACTGTT CCTGCTGGCC GCCTGGACGG CTCGGGCG

SEQ ID NO.3: Nucleotide sequence of SP+C100

ATG CTGCCCGGTT TGGCACTGTT CCTGCTGGCC GCCTGGACGG CTCGGGCGCT G

GATGC AGAATTCCGA CATGACTCAG GATATGAAGT TCATCATCAA AAATTGGTGT

TCTTTGCAGA AGATGTGGGT TCAAACAAAG GTGCAATCAT TGGACTCATG

GTGGGCGGTG TTGTCATAGC GACAGTGATC GTCATCACCT TGGTGATGCT GAAGAAGAAA

CAGTACACAT CCATTCATCA TGGTGTGGTG GAGGTTGACG CCGCTGTCAC CCCAGAGGAG

CGCCACCTGT CCAAGATGCA GCAGAACGGC TACGAAAATC CAACCTACAA GTTCTTTGAG

CAGATGCAGA ACTAG

SEQ ID NO.4: Nucleotide sequence of the 42bp intron

GTATGTTTCGAATGATACTAACATAACATAGAACATTTTCAG

SEQ ID NO.5: Nucleotide sequence of intron+SP+C100

GTATGTTTCGAATGATACTAACATAACATAGAACATTTTCAGGAGGACCCTTGGCTAGCGTCGACGGT

ACCGGGCCCCCCCTCGAGGTCGACGGTATCGATAACCTTCACAGCAGCGCACTCGGTGCCCCGCG

CAGGGTCGCGATG CTGCCCGGTT TGGCACTGTT CCTGCTGGCCGCCTGGACGG CTCGGGCGCT

GGATGC AGAATTCCGAATGACTCAGGATATGAAGTCATCATCAAAAATTGGTGT TCTTTGCAGA

AGATGTGGGT TCAAACAAAG GTGCAATCAT TGGACTCATG GTGGGCGGTG TTGTCATAGC

GACAGTGATC GTCATCACCT TGGTGATGCT GAAGAAGAAA CAGTACACAT CCATTCATCA

TGGTGTGGTG GAGGTTGACG CCGCTGTCAC CCCAGAGGAGCGCCACCTGT CCAAGATGCA

GCAGAACGGC TACGAAAATC CAACCTACAA GTTCTTTGAG CAGATGCAGA ACTAG

SEQ ID NO.6: Nucleotide sequence of unc-119

AAGCTTCAGTAAAAGAAGTAGAATTTTATAGTTTTTTTTCTGTTTGAAAAATTCTCCCCATCAATGTTCT

TTCAAATAAATACATCACTAATGCAAAGTATTCTATAACCTCATATCTAAATTCTTCAAAATCTTAACAT

ATC

TTATCATTGCTTTAAGTCAACGTAACATTAAAAAAAAATGTTTTGGAAAATGTGTCAAGTCTCTCAAAATT

CAGTTTTTTAAACCACTCCTATAGTCCTATAGTCCTATAGTTACCCATGAAATCCTTATATATTACTGTA

AAATGTTTCAAAAACCATTGGCAAATTGCCAGAACTGAAAATTTCCGGCAAATTGGGGAACCGGCAA

ATTGCCAATTTGCTGAATTTGCCGGAAACGGTAATTGCCGAAAGTTTTTGACACGAAAATGGCAAATT

GTGGTTTTAAAATTTTTTTTTTTGGAAATTTCAGAATTTCAATTTTAATCGGCAAAACTGTAGGCATCCT

AAGAATGTTCCTACATCTATTTTGAAAAGTAAGCGAATTAATTCTATGAAAATGTCTAAAGAAAATGGG

GAAACAATTTCAAAAAGGCACAGTTTCAATGGTTTCCGAATTATACTAAATCCCTCTAAAAACTTCCGG

CAAATTGATATCCGTAAAAGAGCAAATCCGCATTTTTGCCGAAAATTAAAATTTCCGACAAATCGGCA

AACCGGCAATTTGGCGAAATTTGCCGGAACGATTGCCGCCCACCCCTGTTCCAGAGGTTCAAACTG

-continued

GTAGCAAAGCTCAAAATTTCTCAAATTCTCCAATTTTTTTTGAATTTTGGCAGTGTACCAAAATGACA

TTCAGTCATATTGGTTTATTATAGATTTATTTAGATAAAATCCTAAATGATTCTACCTTTAAAGATGCCC

ACTTTAAAAGTAATGACTCAAACTTCAAATTGCTCTAAGATTCTATTGAATTACCATCTTTTCCTCTCAT

TTTCTCTCACTGTCTATTTCATCACAAATTCATCCCTCTCTCCTCTCTTCTCTCCCTCTCTCTCTT

TCTCTTTGCTCATCATCTGTCATTTTGTCCGTTCCTCTCTCTGCGCCCTCAGCGTTCCCCACACTCTC

TCGCTTCTCTTTTCCTAGACGTCTTCTTTTTTCATCTTCTTCAGCCTTTTTCGCCATTTTCCATCTCTGT

CAATCATTACGGACGACCCCCATTATCGAT

SEQ ID NO.7: Nucleotide sequence of unc-119+intron+SP+C100

AAGCTTCAGTAAAAGAAGTAGAATTTTATAGTTTTTTTTCTGTTTGAAAAATTCTCCCCATCA

ATGTTCTTTCAAATAAATACATCACTAATGCAAAGTATTCTATAACCTCATATCTAAATTCTTCAAAATC

TTAACATATCTTATCATTGCTTTAAGTCAACGTAACATTAAAAAAAAATGTTTTGGAAAATGTGTCAAGTC

TCTCAAAATTCAGTTTTTTAAACCACTCCTATAGTCCTATAGTCCTATAGTTACCCATGAAATCCTTATA

TATTACTGTAAAATGTTTCAAAAACCATTGGCAAATTGCCAGAACTGAAAATTTCCGGCAAATTGGGG

AACCGGCAAATTGCCAATTTGCTGAATTTGCCGGAAACGGTAATTGCCGAAAGTTTTTGACACGAAAA

TGGCAAATTGTGGTTTTAAAATTTTTTTTTTGGAAATTTCAGAATTTCAATTTTAATCGGCAAAACTGT

AGGCATCCTAAGAATGTTCCTACATCTATTTTGAAAAGTAAGCGAATTAATTCTATGAAAATGTCTAAA

GAAAATGGGGAAACAATTTCAAAAAGGCACAGTTTCAATGGTTTCCGAATTATACTAAATCCCTCTAA

AAACTTCCGGCAAATTGATATCCGTAAAAGAGCAAATCCGCATTTTTGCCGAAAATTAAAATTTCCGA

CAAATCGGCAAACCGGCAATTTGGCGAAATTTGCCGGAACGATTGCCGCCCACCCCTGTTCCAGAG

GTTCAAACTGGTAGCAAAGCTCAAAATTTCTCAAATTCTCCAATTTTTTTTGAATTTTGGCAGTGTAC

CAAAATGACATTCAGTCATATTGGTTTATTATAGATTTATTTAGATAAAATCCTAAATGATTCTACCTTT

AAAGATGCCCACTTTAAAAGTAATGACTCAAACTTCAAATTGCTCTAAGATTCTATTGAATTACCATCT

TTTCCTCTCATTTTCTCTCACTGTCTATTTCATCACAAATTCATCCCTCTCTCCTCTCTTCTCTCTCCCT

CTCTCTCTTTCTCTTTGCTCATCATCTGTCAT

TTTGTCCGTTCCTCTCTCTGCGCCCTCAGCGTTCCCCACACTCTCTCGCTTCTCTTTTCCTAGACGTC

TTCTTTTTTCATCTTCTTCAGCCTTTTTCGCCATTTTCCATCTCTGTCAATCATTACGGACGACCCCCA

TTATCGATAAGATCTCCACGGTGGCCGCGAATTCCTGCAGCCCGGGGGATCCCCGGGATTGGCCAA

AGGACCCAAAGGTATGTTTCGAATGATACTAACATAACATAGAACATTTTCAGGAGGACCCTTGGCTA

GCGTCGACGGTACCGGGCCCCCCCTCGAGGTCGACGGTATCGATAACCTTCACAGCAGCGCACTC

GGTGCCCCGCGCAGGGTCGCGATGCTGCCCGGTT

TGGCACTGTTCCTGCTGGCCGCCTGGACGGCTCGGGCGCTGGATGCAGAATTCCGA

CATGACTCAGGATATGAAGTTCATCATCAAAAATTGGTGTTCTTTGCAGAAGATGTGGGTTCAAACAA

AG GTGCAATCAT TGGACTCATGGTGGGCGGTGTTGTCATAGCGACAGTGATCGTCATCACCT

TGGTGATGCT GAAGAAGAAACAGTACACAT CCATTCATCA TGGTGTGGTG GAGGTTGACG

CCGCTGTCAC CCCAGAGGAGCGCCACCTGT CCAAGATGCA GCAGAACGGC TACGAAAATC

CAACCTACAA GTTCTTTGAGCAGATGCAGA ACTAG

SEQ ID NO.8: Nucleotide sequence of the expression vector

ACCCCCGCCACAGCAGCCTCTGAAGTTGGACACGGATCCACTAGTTCTAGAGCGGCCGCCACCGC

GGTGGAGCTCCGCATCGGCCGCTGTCATCAGATCGCCATCTCGCGCCCGTGCCTCTGACTTCTAAG

TCCAATTACTCTTCAACATCCCTACATGCTCTTTCTCCCTGTGCTCCCACCCCCTATTTTTGTTATTAT

-continued

```
CAAAAAAACTTCTTCTTAATTTCTTTGTTTTTTAGCTTCTTTTAAGTCACCTCTAACAATGAAATTGTGT
AGATTCAAAAATAGAATTAATTCGTAATAAAAAGTCGAAAAAAATTGTGCTCCCTCCCCCCATTAATAA
TAATTCTATCCCAAAATCTACACAATGTTCTGTGTACACTTCTTATGTTTTTTTACTTCTGATAAATTTT
TTTTGAAACATCATAGAAAAAACCGCACACAAAATACCTTATCATATGTTACGTTTCAGTTTATGACCG
CAATTTTTATTTCTTCGCACGTCTGGGCCTCTCATGACGTCAAATCATGCTCATCGTGAAAAAGTTTT
GGAGTATTTTTGGAATTTTTCAATCAAGTGAAAGTTTATGAAATTAATTTTCCTGCTTTTGCTTTTTGGG
GGTTTCCCCTATTGTTTGTCAAGAGTTTCGAGGACGGCGTTTTTCTTGCTAAAATCACAAGTATTGAT
GAGCACGATGCAAGAAAGATCGGAAGAAGGTTTGGGTTTGAGGCTCAGTGGAAGGTGAGTAGAAGT
TGATAATTTGAAAGTGGAGTAGTGTCTATGGGGTTTTTGCCTTAAATGACAGAATACATTCCCAATATA
CCAAACATAACTGTTTCCTACTAGTCGGCCGTACGGGCCCTTTCGTCTCGCGCGTTTCGGTGATGAC
GGTGAAAACCTCTGACACATGCAGCTCCCGGAGACGGTCACAGCTTGTCTGTAAGCGGATGCCGGG
AGCAGACAAGCCCGTCAGGGCGCGTCAGCGGGTGTTGGCGGGTGTCGGGGCTGGCTTAACTATGC
GGCATCAGAGCAGATTGTACTGAGAGTGCACCATATGCGGTGTGAAATACCGCACAGATGCGTAAG
GAGAAAATACCGCATCAGGCGGCCTTAAGGGCCTCGTGATACGCCTATTTTTATAGGTTAATGTCAT
GATAATAATGGTTTCTTAGACGTCAGGTGGCACTTTTCGGGGAAATGTGCGCGGAACCCCTATTTGT
TTATTTTTCTAAATACATTCAAATATGTATCCGCTCATGAGACAATAACCCTGATAAATGCTTCAATAAT
ATTGAAAAGGAAGAGTATGAGTATTCAACATTTCCGTGTCGCCCTTATTCCCTTTTTTGCGGCATTTT
GCCTTCCTGTTTTTGCTC
ACCCAGAAACGCTGGTGAAAGTAAAAGATGCTGAAGATCAGTTGGGTGCACGAGTGGGTTACATCG
AACTGGATCTCAACAGCGGTAAGATCCTTGAGAGTTTTCGCCCCGAAGAACGTTTTCCAATGATGAG
CACTTTTAAAGTTCTGCTATGTGGCGCGGTATTATCCCGTATTGACGCCGGGCAAGAGCAACTCGGT
CGCCGCATACACTATTCTCAGAATGACTTGGTTGAGTACTCACCAGTCACAGAAAAGCATCTTACGG
ATGGCATGACAGTAAGAGAATTATGCAGTGCTGCCATAACCATGAGTGATAACACTGCGGCCAACTT
ACTTCTGACAACGATCGGAGGACCGAAGGAGCTAACCGCTTTTTTGCACAACATGGGGGATCATGTA
ACTCGCCTTGATCGTTGGGAACCGGAGCTGAATGAAGCCATACCAAACGACGAGCGTGACACCACG
ATGCCTGTAGCAATGGCAACAACGTTGCGCAAACTATTAACTGGCGAACTACTTACTCTAGCTTCCC
GGCAACAATTAATAGACTGGATGGAGGCGGATAAAGTTGCAGGACCACTTCTGCGCTCGGCCCTTC
CGGCTGGCTGGTTTATTGCTGATAAATCTGGAGCCGGTGAGCGTGGGTCTCGCGGTATCATTGCAG
CACTGGGGCCAGATGGTAAGCCCTCCCGTATCGTAGTTATCTACACGACGGGGAGTCAGGCAACTA
TGGATGAACGAAATAGACAGATCGCTGAGATAGGTGCCTCACTGATTAAGCATTGGTAACTGTCAGA
CCAAGTTTACTCATATATACTTTAGATTGATTTAAAACTTCATTTTTAATTTAAAAGGATCTAGGTGAAG
ATCCTTTTTGATAATCTCATGACCAAAATCCCTTAACGTGAGTTTTCGTTCCACTGAGCGTCAGACCC
CGTAGAAAAGATCAAAGGATCTTCTTGAGATCCTTTTTTTCTGCGCGTAATCTGCTGCTTGCAAACAA
AAAAACCACCGCTACCAGCGGTGGTTTGTTTGCCGGATCAAGAGCTACCAACTCTTTTTCCGAAGGT
AACTGGCTTCAGCAGAGCGCAGATACCAAATACTGTCCTTCTAGTGTAGCCGTAGTTAGGCCACCAC
TTCAAGAACTCTGTAGCACCGCCTACATACCTCGCTCTGCTAATCCTGTTACCAGTGGCTGCTGCCA
GTGGCGATAAGTCGTGTCTTACCGGGTTGGACTCAAGACGATAGTTACCGGATAAGGCGCAGCGGT
CGGGCTGAACGGGGGGTTCGTGCACACAGCCCAGCTTGGAGCGAACGACCTACACCGAACTGAGA
TACCTACAGCGTGAGCATTGAGAAAGCGCCACGCTTCCCGAAGGGAGAAAGGCGGACAGGTATCCG
GTAAGCGGCAGGGTCGGAACAGGAGAGCGCACGAGGGAGCTTCCAGGGGGAAACGCCTGGTATCT
```

-continued

```
TTATAGTCCTGTCGGGTTTCGCCACCTCTGACTTGAGCGTCGATTTTTGTGATGCTCGTCAGGGGGG
CGGAGCCTATGGAAAAACGCCAGCAACGCGGCCTTTTTACGGTTCCTGGCCTTTTGCTGGCCTTTTG
CTCACATGTTCTTTCCTGCGTTATCCCCTGATTCTGTGGATAACCGTATTACCGCCTTTGAGTGAGCT
GATACCGCTCGCCGCAGCCGAACGACCGAGCGCAGCGAGTCAGTGAGCGAGGAAGCGGAAGAGC
GCCCAATACGCAAACCGCCTCTCCCCGCGCGTTGGCCGATTCATTAATGCAGCTGGCACGACAGGT
TTCCGGACTGGAAAGCGGGCAGTGAGCGCAACGCAATTAATGTGAGTTAGCTCACTCATTAGGCAC
CCCAGGCTTTACACTTTATGCTTCCGGCTCGTATGTTGTGTGGAATTGTGAGCGGATAACAATTTCAC
ACAGGAAACAGCTATGACCATGATTACGCCAAGCTT
```

SEQ ID NO.9: Amino acid sequence of SP

MLPGLALFLL AAWTARA

SEQ ID NO.10: Amino acid sequence of the fusion protein

MLPGLALFLL AAWTARALDA EFRHDSGYEV HHQKLVFFAE DVGSNKGAII
GLMVGGVVIA TVIVITLVML KKKQYTSIHH GVVEVDAAVT PEERHLSKMQ
QNGYENPTYK FFEQMQN

SEQ ID NO. 11: Nucleotide sequence of the vector unc-119-SP-C100

```
ATGACCATGATTACGCCAAGCTTCAGTAAAAGAAGTAGAATTTTATAGTTTTTTTTCTGTTTGAAAAAT
TCTCCCCATCAATGTTCTTTCAAATAAATACATCACTAATGCAAAGTATTCTATAACCTCATATCTAAAT
TCTTCAAAATCTTAACATATCTTATCATTGCTTTAAGTCAACGTAACATTAAAAAAAATGTTTTGGAAAA
TGTGTCAAGTCTCTCAAAATTCAGTTTTTTAAACCACTCCTATAGTCCTATAGTCCTATAGTTACCCAT
GAAATCCTTATATATTACTGTAAAATGTTTCAAAAACCATTGGCAAATTGCCAGAACTGAAAATTTCCG
GCAAATTGGGGAACCGGCAAATTGCCAATTTGCTGAATTTGCCGGAAACGGTAATTGCCGAAAGTTT
TTGACACGAAAATGGCAAATTGTGGTTTTAAAATTTTTTTTTTGGAAATTTCAGAATTTCAATTTTAAT
CGGCAAAACTGTAGGCATCCTAAGAATGTTCCTACATCTATTTTGAAAAGTAAGCGAATTAATTCTAT
GAAAATGTCTAAAGAAAATGGGGAAACAATTTCAAAAAGGCACAGTTTCAATGGTTTCCGAATTATAC
TAAATCCCTCTAAAAACTTCCGGCAAATTGATATCCGTAAAAGAGCAAATCCGCATTTTTGCCGAAAA
TTAAAATTTCCGACAAATCGGCAAACCGGCAATTTGGCGAAATTTGCCGGAACGATTGCCGCCCACC
CCTGTTCCAGAGGTTCAAACTGGTAGCAAAGCTCAAAATTTCTCAAATTCTCCAATTTTTTTTGAATT
TTGGCAGTGTACCAAAATGACATTCAGTCATATTGGTTTATTATAGATTTATTTAGATAAAATCCTAAAT
GATTCTACCTTTAAAGATGCCCACTTTAAAAGTAATGACTCAAACTTCAAATTGCTCTAAGATTCTATT
GAATTACCATCTTTTCCTCTCATTTTCTCTCACTGTCTATTTCATCACAAATTCATCCCTCTCTCCTCTC
TTCTCTCTCCCTCTCTCTCTCTTTCTCTTTGCTCATCATCTGTCATTTTGTCCGTTCCTCTCTCTGCGC
CCTCAGCGTTCCCCACACTCTCTCGCTTCTCTTTTCCTAGACGTCTTCTTTTTTCATCTTCTTCAGCCT
TTTTCGCCATTTTCCATCTCTGTCAATCATTACGGACGACCCCCATTATCGATAAGATCTCCACGGTG
GCCGCGAATTCCTGCAGCCCGGGGGATCCCCGGGATTGGCCAAAGGACCCAAAGGTATGTTTCGAA
TGATACTAACATAACATAGAACATTTTCAGGAGGACCCTTGGCTAGCGTCGACGGTACCGGGCCCCC
CCTCGAGGTCGACGGTATCGATAACCTTCACAGCAGCGCACTCGGTGCCCCGCGCAGGGTCGCGA
TG CTGCCCGGTT TGGCACTGTT CCTGCTGGCCGCCTGGACGG CTCGGGCGCT GGATGC
AGAATTCCGA CATGACTCAG GATATGAAGT TCATCATCAAAAATTGGTGT TCTTTGCAGA
AGATGTGGGT TCAAACAAAG GTGCAATCAT TGGACTCATGGTGGGCGGTG TTGTCATAGC
GACAGTGATC GTCATCACCT TGGTGATGCT GAAGAAGAAACAGTACACAT CCATTCATCA
```

-continued

```
TGGTGTGGTG

GAGGTTGACG CCGCTGTCAC CCCAGAGGAGCGCCACCTGT CCAAGATGCA GCAGAACGGC

TACGAAAATCCAACCTACAATTCTTTGAGCAGATGCAGAACTAGACCCCCGCCACAGCAGCCTCTGA

AGTTGGACACGGATCCACTAGTTCTAGAGCGGCCGCCACCGCGGTGGAGCTCCGCATCGGCCGCT

GTCATCAGATCGCCATCTCGCGCCCGTGCCTCTGACTTCTAAGTCCAATTACTCTTCAACATCCCTAC

ATGCTCTTTCTCCCTGTGCTCCCACCCCCTATTTTTGTTATTATCAAAAAAACTTCTTCTTAATTTCTTT

GTTTTTTAGCTTCTTTTAAGTCACCTCTAACAATGAAATTGTGTAGATTCAAAAATAGAATTAATTCGTA

ATAAAAAGTCGAAAAAAATTGTGCTCCCTCCCCCCATTAATAATAATTCTATCCCAAAATCTACACAAT

GTTCTGTGTACACTTCTTATGTTTTTTTTACTTCTGATAAATTTTTTTTGAAACATCATAGAAAAAACCG

CACACAAAATACCTTATCATATGTTACGTTTCAGTTTATGACCGCAATTTTTATTTCTTCGCACGTCTG

GGCCTCTCATGACGTCAAATCATGCTCATCGTGAAAAAGTTTTGGAGTATTTTTGGAATTTTTCAATCA

AGTGAAAGTTTATGAAATTAATTTTCCTGCTTTTGCTTTTTGGGGGTTTCCCCTATTGTTTGTCAAGAG

TTTCGAGGACGGCGTTTTTCTTGCTAAAATCACAAGTATTGATGAGCACGATGCAAGAAAGATCGGA

AGAAGGTTTGGGTTTGAGGCTCAGTGGAAGGTGAGTAGAAGTTGATAATTTGAAAGTGGAGTAGTGT

CTATGGGGTTTTTGCCTTAAATGACAGAATACATTCCCAATATACCAAACATAACTGTTTCCTACTAGT

CGGCCGTACGGGCCCTTTCGTCTCGCGCGTTTCGGTGATGACGGTGAAAACCTCTGACACATGCAG

CTCCCGGAGACGGTCACAGCTTGTCTGTAAGCGGATGCCGGGAGCAGACAAGCCCGTCAGGGCGC

GTCAGCGGGTGTTGGCGGGTGTCGGGGCTGGCTTAACTATGCGGCATCAGAGCAGATTGTACTGAG

AGTGCACCATATGCGGTGTGAAATACCGCACAGATGCGTAAGGAGAAAATACCGCATCAGGCGGCC

TTAAGGGCCTCGTGATACGCCTATTTTTATAGGTTAATGTCATGATAATAATGGTTTCTTAGACGTCAG

GTGGCACTTTTCGGGGAAATGTGCGCGGAACCCCTATTTGTTTATTTTTCTAAATACATTCAAATATGT

ATCCGCTCATGAGACAATAACCCTGATAAATGCTTCAATAATATTGAAAAAGGAAGAGTATGAGTATT

CAACATTTCCGTGTCGCCCTTATTCCCTTTTTTGCGGCATTTTGCCTTCCTGTTTTTGCTCACCCAGAA

ACGCTGGTGAAAGTAAAAGATGCTGAAGATCAGTTGGGTGCACGAGTGGGTTACATCGAACTGGAT

CTCAACAGCGGTAAGATCCTTGAGAGTTTTCGCCCCGAAGAACGTTTTCCAATGATGAGCACTTTTAA

AGTTCTGCTATGTGGCGCGGTATTATCCCGTATTGACGCCGGGCAAGAGCAACTCGGTCGCCGCAT

ACACTATTCTCAGAATGACTTGGTTGAGTACTCACCAGTCACAGAAAAGCATCTTACGGATGGCATGA

CAGTAAGAGAATTATGCAGTGCTGCCATAACCATGAGTGATAACACTGCGGCCAACTTACTTCTGAC

AACGATCGGAGGACCGAAGGAGCTAACCGCTTTTTTGCACAACATGGGGGATCATGTAACTCGCCTT

GATCGTTGGGAACCGGAGCTGAATGAAGCCATACCAAACGACGAGCGTGACACCACGATGCCTGTA

GCAATGGCAACAACGTTGCGCAAACTATTAACTGGCGAACTACTTACTCTAGCTTCCCGGCAACAAT

TAATAGACTGGATGGAGGCGGATAAAGTTGCAGGACCACTTCTGCGCTCGGCCCTTCCGGCTGGCT

GGTTTATTGCTGATAAATCTGGAGCCGGTGAGCGTGGGTCTCGCGGTATCATTGCAGCACTGGGGC

CAGATGGTAAGCCCTCCCGTATCGTAGTTATCTACACGACGGGGAGTCAGGCAACTATGGATGAAC

GAAATAGACAGATCGCTGAGATAGGTGCCTCACTGATTAAGCATTGGTAACTGTCAGACCAAGTTTA

CTCATATATACTTTAGATTGATTTAAAACTTCATTTTTAATTTAAAAGGATCTAGGTGAAGATCCTTTTT

GATAATCTCATGACCAAAATCCCTTAACGTGAGTTTTCGTTCCACTGAGCGTCAGACCCCGTAGAAAA

GATCAAAGGATCTTCTTGAGATCCTTTTTTTCTGCGCGTAATCTGCTG

CTTGCAAACAAAAAAACCACCGCTACCAGCGGTGGTTTGTTTGCCGGATCAAGAGCTACCAACTCTT

TTTCCGAAGGTAACTGGCTTCAGCAGAGCGCAGATACCAAATACTGTCCTTCTAGTGTAGCCGTAGT
```

-continued

```
TAGGCCACCACTTCAAGAACTCTGTAGCACCGCCTACATACCTCGCTCTGCTAATCCTGTTACCAGT

GGCTGCTGCCAGTGGCGATAAGTCGTGTCTTACCGGGTTGGACTCAAGACGATAGTTACCGGATAA

GGCGCAGCGGTCGGGCTGAACGGGGGGTTCGTGCACACAGCCCAGCTTGGAGCGAACGACCTACA

CCGAACTGAGATACCTACAGCGTGAGCATTGAGAAAGCGCCACGCTTCCCGAAGGGAGAAAGGCG

GACAGGTATCCGGTAAGCGGCAGGGTCGGAACAGGAGAGCGCACGAGGGAGCTTCCAGGGGGAA

ACGCCTGGTATCTTTATAGTCCTGTCGGGTTTCGCCACCTCTGACTTGAGCGTCGATTTTTGTGATGC

TCGTCAGGGGGCGGAGCCTATGGAAAAACGCCAGCAACGCGGCCTTTTTACGGTTCCTGGCCTTT

TGCTGGCCTTTTGCTCACATGTTCTTTCCTGCGTTATCCCCTGATTCTGTGGATAACCGTATTACCGC

CTTTGAGTGAGCTGATACCGCTCGCCGCAGCCGAACGACCGAGCGCAGCGAGTCAGTGAGCGAGG

AAGCGGAAGAGCGCCCAATACGCAAACCGCCTCTCCCCGCGCGTTGGCCGATTCATTAATGCAGCT

GGCACGACAGGTTTCCCGACTGGAAAGCGGGCAGTGAGCGCAACGCAATTAATGTGAGTTAGCTCA

CTCATTAGGCACCCCAGGCTTTACACTTTATGCTTCCGGCTCGTATGTTGTGTGGAATTGTGAGCGG

ATAACAATTTCACACAGGAAACAGCT
```

REFERENCES

Baumeister R (1997) Genes & Function 1, 149
Daigle I, Li C (1993), 90 (24), 12045
Kang, J., Lemaire, H. G., Unterbeck, A., Salbaum J. M., Masters C. L., Grzeschik, K. H., Multhaupt, G., Beyreuther, K., Mueller-Hill, B. (1987) Nature, 325, 733
Kenyon, C., Science (1988) 240, 1448
Korswagen H. C., Durbin, R. M., Smits, M. T., Plasterk, R. H. A. (1996), 93, 14680 Proc Natl Acad Sci USA
Kuwabara, P. E. (1997), Trends in Genetics, 13, 454
Levitan D., Doyle T G, Brousseau D., Lee M K. Thinakaran G., Slunt H H., Sisodia S S. Greenwald I. (1996) Proc Natl Acad Sci USA, 93,14940
Levitan D, Greenwald I (1995) Nature 377, 351
Link C. D. (1995) Proc Natl Acad Sci USA, 92, 9368
Mello, C. and Fire, A., Methods in Cell Biology, Academic Press Vol. 48, pp 451, 1995
Riddle et al. (1997) *C. elegans* II, Cold Spring Harbor Laboratory Press
Rumble, B., Retallack, R., Hilbich, C., Simms, G., Multhaup, G., Martins, R., Hockey, A., Montgomery, P., Beyreuther, K., Masters, C. L., (1989), N. Engl. J. Med., 320, 1446
Scheuner, D., Eckman, C., Jensen, M., Song, X., Citron, M., Suzuki, N., Bird, T., Hardy, M., Hutton, W., Kukull, W., Farson, E., Levy-Lahad, E., Vitanen, M., Peskind, E., Poorkaj, P., Schellenberg, G., Tanzi, R., Wasco, W., Lannfeld, D., Selkoe, D., Younkin, S. G. (1996), Nature Medicine, 2, 864
Shoji M., Golde T E., Ghiso J., Cheung T T., Estus S., Shaffer L M., Cai X-D., McKay D M., Tintner R., Fraggione B., Younkin S G. (1992) Science 258,126
Xiajun Li and Iva Greenwald (1997) Proc Natl Acad Sci USA, 94,12204
Yankner, B. A., Caceres, A., Duffy, L. K. (1990) Proc Natl Acad Sci USA, 87, 9020

What is claimed is:

1. A transgene, comprising:
   a) an isolated polynucleotide encoding an amyloid precursor protein (APP) or a part thereof, wherein the APP peptide or part thereof contains an AB peptide, and wherein the isolated polynucleotide encodes the 100 carboxyterminal amino acids of APP, beginning with the sequence of the AB peptide and ending with the carboxy terminal amino acid of APP (C100 fragment);
   b) a promoter for expression of the transgene in a cell of the nematode *Caenorhabditis elegans* (*C. elegans*); and
   c) an additional coding nucleotide sequence and an additional non-coding nucleotide sequence,
   wherein the APP peptide or part thereof is cleavable by a secretase for identifying and measuring the activity of a secretase, wherein said secretase is gamma-secretase, and wherein the polynucleotide encoding APP or part thereof and the additional coding and noncoding nucleotide sequences comprise SEQ ID NO: 5.

2. A transgene, comprising:
   a) an isolated polynucleotide encoding an amyloid precursor protein (APP) or a part thereof wherein the APP peptide or part thereof contains an AB peptide, and wherein the isolated polynucleotide encodes the 100 carboxyterminal amino acids of APP, beginning with the sequence of the Aβ peptide and ending with the carboxy terminal amino acid of APP (C100 fragment); and
   b) a promoter for expression of the transgene in a cell of the nematode *Caenorhabditis elegans* (*C. elegans*);
   wherein the APP peptide or part thereof is cleavable by a secretase for identifying and measuring the activity of a secretase, wherein said secretase is gamma-secretase, and wherein the promoter has the nucleotide sequence of SEQ ID NO: 6.

3. A transgene, comprising:
   a) an isolated polynucleotide encoding an amyloid precursor protein (APP) or a part thereof, wherein the APP peptide or part thereof contains an Aβ peptide, and wherein the isolated polynucleotide encodes the 100 carboxyterminal amino acids of APP, beginning with the sequence of the Aβ peptide and ending with the carboxy terminal amino acid of APP (C100 fragment;
b) a promoter for expression of the transgene in a cell of the nematode *Caenorhabditis elegans* (*C. elegans*); and
c) an additional coding nucleotide sequence and an additional non-coding nucleotide sequence, wherein the APP peptide or part thereof is cleavable by a secretase for identifying and measuring the activity of a secretase, wherein said secretase is gamma-secretase, and wherein the polynucleotide encoding APP or part thereof, the additional coding and noncoding nucleotide sequences, and the promoter comprises SEQ ID NO: 7.

4. An expression vector which comprises a polynucleotide having the sequence set forth in SEQ ID NO: 8.

* * * * *

SEQUENCE LISTING

```
<160> NUMBER OF SEQ ID NOS: 11

<210> SEQ ID NO 1
<211> LENGTH: 303
<212> TYPE: DNA
<213> ORGANISM: Caenorhabditis elegans

<400> SEQUENCE: 1
ctggatgcag aattccgaca tgactcagga tatgaagttc atcatcaaaa attggtgttc      60
tttgcagaag atgtgggttc aaacaaaggt gcaatcattg gactcatggt gggcggtgtt     120
gtcatagcga cagtgatcgt catcaccttg gtgatgctga agaagaaaca gtacacatcc     180
attcatcatg gtgtggtgga ggttgacgcc gctgtcaccc cagaggagcg ccacctgtcc     240
aagatgcagc agaacggcta cgaaaatcca acctacaagt tctttgagca gatgcagaac     300
tag                                                                   303
```

<210> SEQ ID NO 2
<211> LENGTH: 51
<212> TYPE: DNA
<213> ORGANISM: Caenorhabditis elegans

<400> SEQUENCE: 2
atgctgcccg gtttggcact gttcctgctg gccgcctgga cggctcgggc g        51

<210> SEQ ID NO 3
<211> LENGTH: 354
<212> TYPE: DNA
<213> ORGANISM: Caenorhabditis elegans

<400> SEQUENCE: 3
atgctgcccg gtttggcact gttcctgctg gccgcctgga cggctcgggc gctggatgca        60
gaattccgac atgactcagg atatgaagtt catcatcaaa aattggtgtt ctttgcagaa       120
gatgtgggtt caaacaaagg tgcaatcatt ggactcatgg tgggcggtgt tgtcatagcg       180
acagtgatcg tcatcacctt ggtgatgctg aagaagaaac agtacacatc cattcatcat       240
ggtgtggtgg aggttgacgc cgctgtcacc ccagaggagc gccacctgtc caagatgcag       300
cagaacggct acgaaaatcc aacctacaag ttctttgagc agatgcagaa ctag            354

<210> SEQ ID NO 4
<211> LENGTH: 42
<212> TYPE: DNA
<213> ORGANISM: Caenorhabditis elegans

<400> SEQUENCE: 4
gtatgtttcg aatgatacta acataacata gaacattttc ag                          42

<210> SEQ ID NO 5
<211> LENGTH: 495
<212> TYPE: DNA
<213> ORGANISM: Caenorhabditis elegans

<400> SEQUENCE: 5
gtatgtttcg aatgatacta acataacata gaacattttc aggaggaccc ttggctagcg        60
tcgacggtac cgggcccccc ctcgaggtcg acggtatcga taaccttcac agcagcgcac       120
tcggtgcccc gcgcagggtc gcgatgctgc ccggtttggc actgttcctg ctggccgcct       180
ggacggctcg ggcgctggat gcagaattcc gaatgactca ggatatgaag tcatcatcaa       240
aaattggtgt tctttgcaga gatgtgggt tcaaacaaag gtgcaatcat tggactcatg       300
gtgggcggtg ttgtcatagc gacagtgatc gtcatcacct tggtgatgct gaagaagaaa       360
cagtacacat ccattcatca tggtgtggtg gaggttgacg ccgctgtcac cccagaggag       420
cgccacctgt ccaagatgca gcagaacggc tacgaaaatc caacctacaa gttctttgag       480
cagatgcaga actag                                                       495

<210> SEQ ID NO 6
<211> LENGTH: 1207
<212> TYPE: DNA
<213> ORGANISM: Caenorhabditis elegans

<400> SEQUENCE: 6
aagcttcagt aaagaagta gaatttata gtttttttc tgtttgaaaa attctcccca        60
tcaatgttct ttcaaataaa tacatcacta atgcaaagta ttctataacc tcatatctaa       120
attcttcaaa atcttaacat atcttatcat tgctttaagt caacgtaaca ttaaaaaaaa       180

```
tgttttggaa aatgtgtcaa gtctctcaaa attcagtttt ttaaaccact cctatagtcc      240
tatagtccta tagttaccca tgaaatcctt atatattact gtaaaatgtt tcaaaaacca      300
ttggcaaatt gccagaactg aaaatttccg gcaaattggg gaaccggcaa attgccaatt      360
tgctgaattt gccggaaacg gtaattgccg aaagttttg acacgaaaat ggcaaattgt       420
ggttttaaaa tttttttttt tggaaatttc agaatttcaa ttttaatcgg caaaactgta      480
ggcatcctaa gaatgttcct acatctattt tgaaaagtaa gcgaattaat tctatgaaaa      540
tgtctaaaga aaatggggaa acaatttcaa aaaggcacag tttcaatggt ttccgaatta      600
tactaaatcc ctctaaaaac ttccggcaaa ttgatatccg taaaagagca aatccgcatt      660
tttgccgaaa attaaaattt ccgacaaatc ggcaaaccgg caatttggcg aaatttgccg      720
gaacgattgc cgcccacccc tgttccagag gttcaaactg gtagcaaagc tcaaaatttc      780
tcaaattctc caattttttt ttgaattttg gcagtgtacc aaaatgacat tcagtcatat      840
tggtttatta tagatttatt tagataaaat cctaaatgat tctacctta aagatgccca      900 ctttaaaagt aatgactcaa acttcaaatt gctctaagat tctattgaat taccatcttt      960
tcctctcatt ttctctcact gtctatttca tcacaaattc atccctctct cctctcttct     1020
ctctccctct ctctctcttt tctttgctc atcatctgtc attttgtccg ttcctctctc      1080
tgcgccctca gcgttcccca cactctctcg cttctctttt cctagacgtc ttctttttc      1140 atcttcttca gccttttcg ccatttccca tctctgtcaa tcattacgga cgaccccat      1200 tatcgat                                                               1207

<210> SEQ ID NO 7
<211> LENGTH: 1773
<212> TYPE: DNA
<213> ORGANISM: Caenorhabditis elegans

<400> SEQUENCE: 7
aagcttcagt aaaagaagta gaattttata gttttttttc tgtttgaaaa attctcccca       60
tcaatgttct ttcaaataaa tacatcacta atgcaaagta ttctataacc tcatatctaa      120
attcttcaaa atcttaacat atcttatcat tgctttaagt caacgtaaca ttaaaaaaaa      180
tgttttggaa aatgtgtcaa gtctctcaaa attcagtttt ttaaaccact cctatagtcc      240
tatagtccta tagttaccca tgaaatcctt atatattact gtaaaatgtt tcaaaaacca      300
ttggcaaatt gccagaactg aaaatttccg gcaaattggg gaaccggcaa attgccaatt      360
tgctgaattt gccggaaacg gtaattgccg aaagttttg acacgaaaat ggcaaattgt       420
ggttttaaaa tttttttttt tggaaatttc agaatttcaa ttttaatcgg caaaactgta      480
ggcatcctaa gaatgttcct acatctattt tgaaaagtaa gcgaattaat tctatgaaaa      540
tgtctaaaga aaatggggaa acaatttcaa aaaggcacag tttcaatggt ttccgaatta      600
tactaaatcc ctctaaaaac ttccggcaaa ttgatatccg taaaagagca aatccgcatt      660
tttgccgaaa attaaaattt ccgacaaatc ggcaaaccgg caatttggcg aaatttgccg      720
gaacgattgc cgcccacccc tgttccagag gttcaaactg gtagcaaagc tcaaaatttc      780
tcaaattctc caattttttt ttgaattttg gcagtgtacc aaaatgacat tcagtcatat      840
tggtttatta tagatttatt tagataaaat cctaaatgat tctacctta aagatgccca      900 ctttaaaagt aatgactcaa acttcaaatt gctctaagat tctattgaat taccatcttt      960
tcctctcatt ttctctcact gtctatttca tcacaaattc atccctctct cctctcttct     1020
```

-continued

| | | | | |
|---|---|---|---|---|
| ctctccctct | ctctctcttt | tctttgctc | atcatctgtc | attttgtccg | ttcctctctc | 1080 |
| tgcgccctca | gcgttcccca | cactctctcg | cttctctttt | cctagacgtc | ttcttttttc | 1140 |
| atcttcttca | gcctttttcg | ccattttcca | tctctgtcaa | tcattacgga | cgaccccat | 1200 |
| tatcgataag | atctccacgg | tggccgcgaa | ttcctgcagc | ccgggggatc | ccgggattg | 1260 |
| gccaaaggac | ccaaaggtat | gtttcgaatg | atactaacat | aacatagaac | attttcagga | 1320 |
| ggacccttgg | ctagcgtcga | cggtaccggg | ccccccctcg | aggtcgacgg | tatcgataac | 1380 |
| cttcacagca | gcgcactcgg | tgccccgcgc | agggtcgcga | tgctgcccgg | tttggcactg | 1440 |
| ttcctgctgg | ccgcctggac | ggctcgggcg | ctggatgcag | aattccgaca | tgactcagga | 1500 |
| tatgaagttc | atcatcaaaa | attggtgttc | tttgcagaag | atgtgggttc | aaacaaaggt | 1560 |
| gcaatcattg | gactcatggt | gggcggtgtt | gtcatagcga | cagtgatcgt | catcaccttg | 1620 |
| gtgatgctga | agaagaaaca | gtacacatcc | attcatcatg | gtgtggtgga | ggttgacgcc | 1680 |
| gctgtcaccc | cagaggagcg | ccacctgtcc | aagatgcagc | agaacggcta | cgaaaatcca | 1740 |
| acctacaagt | tctttgagca | gatgcagaac | tag | | | 1773 |

<210> SEQ ID NO 8
<211> LENGTH: 3344
<212> TYPE: DNA
<213> ORGANISM: Caenorhabditis elegans

<400> SEQUENCE: 8

| | | | | |
|---|---|---|---|---|
| acccccgcca | cagcagcctc | tgaagttgga | cacggatcca | ctagttctag | agcggccgcc | 60 |
| accgcggtgg | agctccgcat | cggccgctgt | catcagatcg | ccatctcgcg | cccgtgcctc | 120 |
| tgacttctaa | gtccaattac | tcttcaacat | ccctacatgc | tctttctccc | tgtgctccca | 180 |
| cccctattt | ttgttattat | caaaaaaact | tcttcttaat | ttctttgttt | tttagcttct | 240 |
| tttaagtcac | ctctaacaat | gaaattgtgt | agattcaaaa | atagaattaa | ttcgtaataa | 300 |
| aaagtcgaaa | aaaattgtgc | tccctccccc | cattaataat | aattctatcc | caaaatctac | 360 |
| acaatgttct | gtgtacactt | cttatgtttt | ttttacttct | gataaatttt | ttttgaaaca | 420 |
| tcatagaaaa | aaccgcacac | aaaataccct | atcatatgtt | acgtttcagt | ttatgaccgc | 480 |
| aatttttatt | tcttcgcacg | tctgggcctc | tcatgacgtc | aaatcatgct | catcgtgaaa | 540 |
| aagttttgga | gtattttttgg | aattttttcaa | tcaagtgaaa | gtttatgaaa | ttaattttcc | 600 |
| tgcttttgct | ttttgggggt | ttcccctatt | gtttgtcaag | agtttcgagg | acggcgtttt | 660 |
| tcttgctaaa | atcacaagta | ttgatgagca | cgatgcaaga | aagatcggaa | gaaggtttgg | 720 |
| gtttgaggct | cagtggaagg | tgagtagaag | ttgataattt | gaaagtggag | tagtgtctat | 780 |
| ggggtttttg | ccttaaatga | cagaatacat | tcccaatata | ccaaacataa | ctgtttccta | 840 |
| ctagtcggcc | gtacgggccc | tttcgtctcg | cgcgtttcgg | tgatgacggt | gaaaacctct | 900 |
| gacacatgca | gctcccggag | acgtcacag | cttgtctgta | agcggatgcc | gggagcagac | 960 |
| aagcccgtca | gggcgcgtca | gcgggtgttg | gcgggtgtcg | gggctggctt | aactatgcgg | 1020 |
| catcagagca | gattgtactg | agagtgcacc | atatgcggtg | tgaaataccg | cacagatgcg | 1080 |
| taaggagaaa | ataccgcatc | aggcggcctt | aagggcctcg | tgatacgcct | attttttatag | 1140 |
| gttaatgtca | tgataataat | ggtttcttag | acgtcaggtg | gcacttttcg | gggaaatgtg | 1200 |
| cgcggaaccc | ctatttgttt | atttttctaa | atacattcaa | atatgtatcc | gctcatgaga | 1260 |
| caataaccct | gataaatgct | tcaataatat | tgaaaaagga | agagtatgag | tattcaacat | 1320 |
| ttccgtgtcg | cccttattcc | cttttttgcg | gcattttgcc | ttcctgtttt | tgctcaccca | 1380 |

```
gaaacgctgg tgaaagtaaa agatgctgaa gatcagttgg gtgcacgagt gggttacatc   1440
gaactggatc tcaacagcgg taagatcctt gagagttttc gccccgaaga acgttttcca   1500
atgatgagca cttttaaagt tctgctatgt ggcgcggtat tatcccgtat tgacgccggg   1560
caagagcaac tcggtcgccg catacactat tctcagaatg acttggttga gtactcacca   1620
gtcacagaaa agcatcttac ggatggcatg acagtaagag aattatgcag tgctgccata   1680
accatgagtg ataacactgc ggccaactta cttctgacaa cgatcggagg accgaaggag   1740
ctaaccgctt ttttgcacaa catggggggat catgtaactc gccttgatcg ttgggaaccg   1800
```

```
gaaacgctgg tgaaagtaaa agatgctgaa gatcagttgg gtgcacgagt gggttacatc   1440
gaactggatc tcaacagcgg taagatcctt gagagttttc gccccgaaga acgttttcca   1500
atgatgagca cttttaaagt tctgctatgt ggcgcggtat tatcccgtat tgacgccggg   1560
caagagcaac tcggtcgccg catacactat tctcagaatg acttggttga gtactcacca   1620
gtcacagaaa agcatcttac ggatggcatg acagtaagag aattatgcag tgctgccata   1680
accatgagtg ataacactgc ggccaactta cttctgacaa cgatcggagg accgaaggag   1740
ctaaccgctt ttttgcacaa catggggggat catgtaactc gccttgatcg ttgggaaccg   1800
gagctgaatg aagccatacc aaacgacgag cgtgacacca cgatgcctgt agcaatggca   1860
acaacgttgc gcaaactatt aactggcgaa ctacttactc tagcttcccg gcaacaatta   1920
atagactgga tggaggcgga taaagttgca ggaccacttc tgcgctcggc ccttccggct   1980
ggctggttta ttgctgataa atctggagcc ggtgagcgtg gtctcgcgg tatcattgca   2040 gcactgggcc agatggtaag ccctcccgta tcgtagttat ctacacgacg gggagtcagg   2100
caactatgga tgaacgaaat agacagatcg ctgagatagg tgcctcactg attaagcatt   2160
ggtaactgtc agaccaagtt tactcatata tactttagat tgatttaaaa cttcattttt   2220
aatttaaaag gatctaggtg aagatccttt ttgataatct catgaccaaa atcccttaac   2280
gtgagttttc gttccactga gcgtcagacc ccgtagaaaa gatcaaagga tcttcttgag   2340
atcctttttt tctgcgcgta atctgctgct tgcaaacaaa aaaaccaccg ctaccagcgg   2400
tggtttgttt gccggatcaa gagctaccaa ctcttttcc gaaggtaact ggcttcagca   2460
gagcgcagat accaaatact gtccttctag tgtagccgta gttaggccac cacttcaaga   2520
actctgtagc accgcctaca tacctcgctc tgctaatcct gttaccagtg ctgctgcca   2580 gtggcgataa gtcgtgtctt accgggttgg actcaagacg atagttaccg gataaggcgc   2640
agcggtcggg ctgaacgggg ggttcgtgca cacagcccag cttggagcga acgacctaca   2700
ccgaactgag atacctacag cgtgagcatt gagaaagcgc cacgcttccc gaagggagaa   2760
aggcggacag gtatccggta agcggcaggg tcggaacagg agagcgcacg agggagcttc   2820 caggggaaa cgcctggtat ctttatagtc ctgtcgggtt tcgccacctc tgacttgagc   2880
gtcgattttt gtgatgctcg tcagggggc ggagcctatg gaaaaacgcc agcaacgcgg   2940 ccttttttacg gttcctggcc ttttgctggc cttttgctca catgttcttt cctgcgttat   3000
cccctgattc tgtggataac cgtattaccg cctttgagtg agctgatacc gctcgccgca   3060
gccgaacgac cgagcgcagc gagtcagtga gcgaggaagc ggaagagcgc ccaatacgca   3120
aaccgcctct ccccgcgcgt tggccgattc attaatgcag ctggcacgac aggtttcccg   3180
actggaaagc gggcagtgag cgcaacgcaa ttaatgtgag ttagctcact cattaggcac   3240
cccaggcttt acactttatg cttccggctc gtatgttgtg tggaattgtg agcggataac   3300
aatttcacac aggaaacagc tatgaccatg attacgccaa gctt              3344
```

<210> SEQ ID NO 9
<211> LENGTH: 17
<212> TYPE: PRT
<213> ORGANISM: Caenorhabditis elegans

<400> SEQUENCE: 9

Met Leu Pro Gly Leu Ala Leu Phe Leu Leu Ala Ala Trp Thr Ala Arg
 1               5                  10                  15

Ala

<210> SEQ ID NO 10
<211> LENGTH: 117
<212> TYPE: PRT
<213> ORGANISM: Caenorhabditis elegans

<400> SEQUENCE: 10

```
Met Leu Pro Gly Leu Ala Leu Phe Leu Leu Ala Ala Trp Thr Ala Arg
  1               5                  10                  15

Ala Leu Asp Ala Glu Phe Arg His Asp Ser Gly Tyr Glu Val His His
             20                  25                  30

Gln Lys Leu Val Phe Phe Ala Glu Asp Val Gly Ser Asn Lys Gly Ala
         35                  40                  45

Ile Ile Gly Leu Met Val Gly Gly Val Val Ile Ala Thr Val Ile Val
 50                  55                  60

Ile Thr Leu Val Met Leu Lys Lys Lys Gln Tyr Thr Ser Ile His His
 65                  70                  75                  80

Gly Val Val Glu Val Asp Ala Ala Val Thr Pro Glu Glu Arg His Leu
                 85                  90                  95

Ser Lys Met Gln Gln Asn Gly Tyr Glu Asn Pro Thr Tyr Lys Phe Phe
            100                 105                 110

Glu Gln Met Gln Asn
        115
```

<210> SEQ ID NO 11
<211> LENGTH: 5109
<212> TYPE: DNA
<213> ORGANISM: Caenorhabditis elegans

<400> SEQUENCE: 11

| | | | | | |
|---|---|---|---|---|---|
| atgaccatga | ttacgccaag | cttcagtaaa | agaagtagaa | ttttatagtt | ttttttctgt | 60 |
| ttgaaaaatt | ctccccatca | atgttctttc | aaataaatac | atcactaatg | caaagtattc | 120 |
| tataacctca | tatctaaatt | cttcaaaatc | ttaacatatc | ttatcattgc | tttaagtcaa | 180 |
| cgtaacatta | aaaaaaatgt | tttggaaaat | gtgtcaagtc | tctcaaaatt | cagttttta | 240 |
| aaccactcct | atagtcctat | agtcctatag | ttacccatga | aatccttata | tattactgta | 300 |
| aaatgtttca | aaaaccattg | gcaaattgcc | agaactgaaa | atttccggca | aattggggaa | 360 |
| ccggcaaatt | gccaatttgc | tgaatttgcc | ggaaacggta | attgccgaaa | gttttgaca | 420 |
| cgaaaatggc | aaattgtggt | tttaaaattt | ttttttttgg | aaatttcaga | atttcaattt | 480 |
| taatcggcaa | aactgtaggc | atcctaagaa | tgttcctaca | tctatttga | aaagtaagcg | 540 |
| aattaattct | atgaaaatgt | ctaaagaaaa | tggggaaaca | atttcaaaaa | ggcacagttt | 600 |
| caatggtttc | cgaattatac | taaatccctc | taaaaacttc | cggcaaattg | atatccgtaa | 660 |
| aagagcaaat | ccgcattttt | gccgaaaatt | aaaatttccg | acaaatcggc | aaaccggcaa | 720 |
| tttggcgaaa | tttgccggaa | cgattgccgc | ccaccctgt | tccagaggtt | caaactggta | 780 |
| gcaaagctca | aaatttctca | aattctccaa | ttttttttg | aatttggca | gtgtaccaaa | 840 |
| atgacattca | gtcatattgg | tttattatag | atttatttag | ataaaatcct | aaatgattct | 900 |
| acctttaaag | atgcccactt | taaagtaat | gactcaaact | tcaaattgct | ctaagattct | 960 |
| attgaattac | catcttttcc | tctcattttc | tctcactgtc | tatttcatca | caaattcatc | 1020 |
| cctctctcct | ctcttctctc | tccctctctc | tctctttctc | tttgctcatc | atctgtcatt | 1080 |
| ttgtccgttc | ctctctctgc | gccctcagcg | ttccccacac | tctctcgctt | ctctttcct | 1140 |

-continued

```
agacgtcttc ttttttcatc ttcttcagcc ttttttcgcca ttttccatct ctgtcaatca    1200
ttacggacga cccccattat cgataagatc tccacggtgg ccgcgaattc ctgcagcccg    1260
ggggatcccc gggattggcc aaaggaccca aaggtatgtt tcgaatgata ctaacataac    1320
atagaacatt ttcaggagga cccttggcta gcgtcgacgg taccgggccc ccctcgagg    1380 tcgacggtat cgataacctt cacagcagcg cactcggtgc cccgcgcagg gtcgcgatgc    1440
tgcccggttt ggcactgttc ctgctggccg cctggacggc tcgggcgctg gatgcagaat    1500
tccgacatga ctcaggatat gaagttcatc atcaaaaatt ggtgttcttt gcagaagatg    1560
tgggttcaaa caaggtgca atcattggac tcatggtggg cggtgttgtc atagcgacag    1620
tgatcgtcat caccttggtg atgctgaaga agaaacagta cacatccatt catcatggtg    1680
tggtggaggt tgacgccgct gtcaccccag aggagcgcca cctgtccaag atgcagcaga    1740
acggctacga aaatccaacc tacaattctt tgagcagatg cagaactaga cccccgccac    1800
agcagcctct gaagttggac acggatccac tagttctaga gcggccgcca ccgcggtgga    1860
gctccgcatc ggccgctgtc atcagatcgc catctcgcgc ccgtgcctct gacttctaag    1920
tccaattact cttcaacatc cctacatgct cttttctccct gtgctcccac ccctatttt    1980 tgttattatc aaaaaaactt cttcttaatt tctttgtttt tagcttcttt taagtcacct    2040
ctaacaatga aattgtgtag attcaaaaat agaattaatt cgtaataaaa agtcgaaaaa    2100
aattgtgctc cctcccccca ttaataataa ttctatccca aaatctacac aatgttctgt    2160
gtacacttct tatgttttttt ttacttctga taaattttt ttgaaacatc atagaaaaaa    2220
ccgcacacaa aataccttat catatgttac gtttcagttt atgaccgcaa tttttatttc    2280
ttcgcacgtc tgggcctctc atgacgtcaa atcatgctca tcgtgaaaaa gttttggagt    2340 attttttggaa tttttcaatc aagtgaaagt ttatgaaatt aatttttcctg cttttgcttt    2400 ttgggggttt cccctattgt ttgtcaagag tttcgaggac ggcgttttc ttgctaaaat    2460 cacaagtatt gatgagcacg atgcaagaaa gatcggaaga aggtttgggt ttgaggctca    2520
gtggaaggta gtagaagtt gataatttga agtggagta gtgtctatgg ggttttttgcc    2580 ttaaatgaca gaatacattc ccaatatacc aaacataact gtttcctact agtcggccgt    2640 acgggcccctt tcgtctcgcg cgtttcggtg atgacggtga aaacctctga cacatgcagc    2700
tcccggagac ggtcacagct tgtctgtaag cggatgccgg gagcagacaa gcccgtcagg    2760
gcgcgtcagc gggtgttggc gggtgtcggg gctggcttaa ctatgcggca tcagagcaga    2820
ttgtactgag agtgcaccat atgcggtgtg aaataccgca cagatgcgta aggagaaaat    2880
accgcatcag gcgccttaa gggcctcgtg atacgcctat ttttataggt taatgtcatg    2940
ataataatgg tttcttagac gtcaggtggc acttttcggg gaaatgtgcg cggaacccct    3000
atttgtttat ttttctaaat acattcaaat atgtatccgc tcatgagaca ataaccctga    3060
taaatgcttc aataatattg aaaaggaag agtatgagta ttcaacattt ccgtgtcgcc    3120
cttattccct ttttttgcggc attttgcctt cctgttttttg ctcacccaga aacgctggtg    3180
aaagtaaaag atgctgaaga tcagttgggt gcacgagtgg gttacatcga actggatctc    3240
aacagcggta agatccttga gagttttcgc cccgaagaac gttttccaat gatgagcact    3300
tttaaagttc tgctatgtgg cgcggtatta tcccgtattg acgccgggca agagcaactc    3360
ggtcgccgca tacactattc tcagaatgac ttggttgagt actcaccagt cacagaaaag    3420
catcttacgg atggcatgac agtaagagaa ttatgcagtg ctgccataac catgagtgat    3480
aacactgcgg ccaacttact tctgacaacg atcggaggac cgaaggagct aaccgctttt    3540
```

```
ttgcacaaca tggggatca tgtaactcgc cttgatcgtt gggaaccgga gctgaatgaa   3600
gccataccaa acgacgagcg tgacaccacg atgcctgtag caatggcaac aacgttgcgc   3660
aaactattaa ctggcgaact acttactcta gcttcccggc aacaattaat agactggatg   3720
gaggcggata aagttgcagg accacttctg cgctcggccc ttccggctgg ctggtttatt   3780
gctgataaat ctggagccgg tgagcgtggg tctcgcggta tcattgcagc actggggcca   3840
gatggtaagc cctcccgtat cgtagttatc tacacgacgg ggagtcaggc aactatggat   3900
gaacgaaata gacagatcgc tgagataggt gcctcactga ttaagcattg gtaactgtca   3960
gaccaagttt actcatatat actttagatt gatttaaaac ttcatttttta atttaaaagg   4020 atctaggtga agatcctttt tgataatctc atgaccaaaa tcccttaact gagttttcgt   4080
tccactgagc gtcagacccc gtagaaaaga tcaaaggatc ttcttgagat ccttttttc    4140 tgcgcgtaat ctgctgcttg caaacaaaaa aaccaccgct accagcggtg gtttgtttgc   4200
cggatcaaga gctaccaact cttttccga aggtaactgg cttcagcaga gcgcagatac    4260
caaatactgt ccttctagtg tagccgtagt taggccacca cttcaagaac tctgtagcac   4320
cgcctacata cctcgctctg ctaatcctgt taccagtggc tgctgccagt ggcgataagt   4380
cgtgtcttac cgggttggac tcaagacgat agttaccgga taaggcgcag cggtcgggct   4440 gaacggggg ttcgtgcaca cagcccagct tggagcgaac gacctacacc gaactgagat    4500
acctacagcg tgagcattga gaaagcgcca cgcttcccga agggagaaag gcggacaggt   4560
atccggtaag cggcagggtc ggaacaggag agcgcacgag ggagcttcca gggggaaacg   4620
cctggtatct ttatagtcct gtcgggtttc gccacctctg acttgagcgt cgatttttgt   4680
gatgctcgtc agggggcgg agcctatgga aaaacgccag caacgcggcc ttttttacggt   4740 tcctggcctt ttgctggcct tttgctcaca tgttctttcc tgcgttatcc cctgattctg   4800
tggataaccg tattaccgcc tttgagtgag ctgataccgc tcgccgcagc cgaacgaccg   4860
agcgcagcga gtcagtgagc gaggaagcgg aagagcgccc aatacgcaaa ccgcctctcc   4920
ccgcgcgttg gccgattcat taatgcagct ggcacgacag gtttcccgac tggaaagcgg   4980
gcagtgagcg caacgcaatt aatgtgagtt agctcactca ttaggcaccc caggctttac   5040
actttatgct tccggctcgt atgttgtgtg gaattgtgag cggataacaa tttcacacag   5100
gaaacagct                                                          5109
```